US011534523B2

(12) United States Patent
Wibaux et al.

(10) Patent No.: US 11,534,523 B2
(45) Date of Patent: Dec. 27, 2022

(54) SILICONE ABSORBENT ADHESIVE LAYER

(75) Inventors: Anne Marie Wibaux, Cleveland Heights, OH (US); Vicky Van De Pol, Turnhout (BE)

(73) Assignee: Avery Dennison Corporation, Mentor, OH (US)

( * ) Notice: Subject to any disclaimer, the term of this patent is extended or adjusted under 35 U.S.C. 154(b) by 799 days.

(21) Appl. No.: 14/240,617

(22) PCT Filed: Aug. 29, 2012

(86) PCT No.: PCT/US2012/052745
§ 371 (c)(1),
(2), (4) Date: Feb. 24, 2014

(87) PCT Pub. No.: WO2013/033131
PCT Pub. Date: Mar. 7, 2013

(65) Prior Publication Data
US 2014/0194838 A1 Jul. 10, 2014

Related U.S. Application Data

(60) Provisional application No. 61/529,073, filed on Aug. 30, 2011.

(51) Int. Cl.
| A61L 15/22 | (2006.01) |
| A61F 13/02 | (2006.01) |
| A61L 24/00 | (2006.01) |
| A61L 15/58 | (2006.01) |
| C09J 7/38 | (2018.01) |
| C09J 7/22 | (2018.01) |
| C09J 189/06 | (2006.01) |
| C09J 183/04 | (2006.01) |
| C09J 105/06 | (2006.01) |
| C09J 105/04 | (2006.01) |
| C09J 191/06 | (2006.01) |
| C09J 101/28 | (2006.01) |
| C09J 103/02 | (2006.01) |
| C09J 105/00 | (2006.01) |
| C08L 1/00 | (2006.01) |

(52) U.S. Cl.
CPC ........ *A61L 15/225* (2013.01); *A61F 13/0216* (2013.01); *A61L 15/58* (2013.01); *A61L 15/585* (2013.01); *A61L 24/0094* (2013.01); *C09J 7/22* (2018.01); *C09J 7/38* (2018.01); *C08L 1/00* (2013.01); *C09J 101/286* (2013.01); *C09J 103/02* (2013.01); *C09J 105/00* (2013.01); *C09J 105/04* (2013.01); *C09J 105/06* (2013.01); *C09J 183/04* (2013.01); *C09J 189/06* (2013.01); *C09J 191/06* (2013.01); *C09J 2401/00* (2013.01); *C09J 2483/00* (2013.01)

(58) Field of Classification Search
None
See application file for complete search history.

(56) References Cited

U.S. PATENT DOCUMENTS

| 4,882,377 A | 11/1989 | Sweet et al. |
| 4,987,169 A | 1/1991 | Kuwata et al. |
| 5,599,533 A | 2/1997 | Stepniewski et al. |
| 5,654,362 A | 8/1997 | Schulz, Jr. et al. |
| 5,811,487 A | 9/1998 | Schulz, Jr. et al. |
| 5,880,210 A | 3/1999 | Schulz, Jr. et al. |
| 5,889,108 A | 3/1999 | Zhang |
| 5,929,164 A | 7/1999 | Zhang |
| 5,948,855 A | 9/1999 | Fin et al. |
| 5,969,035 A | 10/1999 | Meinhardt et al. |
| 5,977,280 A | 11/1999 | Kadlec et al. |
| 5,994,459 A | 11/1999 | Berg et al. |
| 6,015,858 A | 1/2000 | Gornowicz |
| 6,027,738 A | 2/2000 | Stepniewski et al. |
| 6,080,394 A | 6/2000 | Lin et al. |
| 6,168,782 B1 | 1/2001 | Lin et al. |
| 6,177,071 B1 | 1/2001 | Lin et al. |
| 6,200,581 B1 | 3/2001 | Lin et al. |
| 6,207,717 B1 | 3/2001 | Lin et al. |
| 6,221,927 B1 | 4/2001 | Lin et al. |
| 6,221,979 B1 | 4/2001 | Lin et al. |
| 6,238,657 B1 | 5/2001 | Lin et al. |
| 6,346,583 B1 | 2/2002 | Kilgour et al. |
| 6,444,745 B1 | 9/2002 | Kilgour et al. |
| 6,538,061 B2 | 3/2003 | Chaiyawat et al. |
| 6,746,765 B1 | 6/2004 | Fattman |
| 2002/0169405 A1* | 11/2002 | Roberts ........................... 602/54 |
| 2003/0130427 A1* | 7/2003 | Cleary ................. A61K 9/7053 525/192 |
| 2004/0228821 A1 | 11/2004 | Sunkel et al. |

(Continued)

FOREIGN PATENT DOCUMENTS

| EP | 0524776 A1 | 1/1993 |
| WO | 02087645 A1 | 11/2002 |
| WO | 2008154546 A2 | 12/2008 |
| WO | 2011039675 A2 | 4/2011 |
| WO | 2013/025955 | 2/2013 |

OTHER PUBLICATIONS

International Search Report and Written Opinion of the International Searching Authority, or the Declaration, dated Feb. 11, 2013.

*Primary Examiner* — Robert A Wax
*Assistant Examiner* — Randeep Singh

(57) ABSTRACT

An adhesive composition comprising silicone adhesives and one or more absorbent fillers such as hydrocolloids is disclosed. The adhesive composition is particularly well suited for use in negative pressure wound therapies.

28 Claims, No Drawings

(56) References Cited

U.S. PATENT DOCUMENTS

| | | | |
|---|---|---|---|
| 2004/0241215 A1* | 12/2004 | Lipman | A61F 13/0246 424/445 |
| 2006/0141016 A1* | 6/2006 | Sambasivam | A61K 36/81 424/445 |
| 2010/0041758 A1* | 2/2010 | Nishiura | A61K 9/7053 514/570 |
| 2010/0322996 A1 | 12/2010 | Wibaux et al. | |
| 2011/0144599 A1* | 6/2011 | Croizat | A61F 13/02 604/313 |

* cited by examiner

SILICONE ABSORBENT ADHESIVE LAYER

CROSS REFERENCE TO RELATED APPLICATION

The present application is a 371 of International Application No. PCT/US2012/052745, which was published in English on Mar. 7, 2013, which claims priority to U.S. Provisional Patent Application No. 61/529,073 filed Aug. 30, 2011, which is incorporated herein by reference in its entirety.

FIELD

The present subject matter relates to adhesive compositions and particularly which are suitable for medical applications such as in contacting skin.

BACKGROUND

A variety of skin contacting adhesives are known to include a pressure sensitive adhesive elastomeric matrix in which water absorbing and water swellable particles of hydrocolloids are dispersed. The pressure sensitive adhesive matrix adheres to skin and contributes to the cohesion of the adhesive. The water absorbing properties of the hydrocolloids enable adhesion to moist skin by removing moisture from the surface. As the hydrocolloids constantly absorb moisture emanating from the skin or originating from exuding wounds, the hydrocolloids also contribute to good adherence over extended periods of time and also prevent maceration of the skin.

In many applications, the adhesive agents will come into contact with body fluids of different types such as feces, urine, wound exudates, and sweat for example. Existing skin adhesives often suffer from a drawback that their adhesiveness is destroyed by contact with body fluids. In order to compensate for this, more aggressive adhesives are used in many applications. These overly aggressive adhesives then create their own issues with respect to skin irritation and even destruction of the outer skin layer, especially in the young and elderly. This is particularly seen in applications where repositionability is desired and where visual wound inspection is required since the dressing is removed and reapplied multiple times creating additional skin irritation problems. Further, portions of the adhesive being in direct contact with the skin or which are exposed to body fluids will gradually swell due to the water absorbing and water swelling properties of the hydrocolloids which will eventually cause disintegration of the adhesive matrix.

Although satisfactory in many regards, a need remains for an improved pressure sensitive adhesive which can be used in skin-contacting applications.

SUMMARY

The difficulties and drawbacks associated with previously known compositions are addressed in the present compositions, articles, and related methods.

In one aspect, the present subject matter provides an adhesive composition comprising a polysiloxane adhesive, and one or more absorbent fillers dispersed in the polysiloxane adhesive.

In another aspect, the subject matter provides an article comprising a layer of an adhesive composition comprising (i) a polysiloxane adhesive and (ii) one or more absorbent fillers dispersed in the polysiloxane adhesive.

In another aspect, the subject matter provides a method of sealingly securing an article to a substrate. The method comprises providing an adhesive composition including (i) a polysiloxane adhesive, and (ii) one or more absorbent fillers dispersed in the polysiloxane adhesive. And, the method also comprises forming a layer of the adhesive composition between the article and the substrate.

In yet another aspect, the present subject matter provides a method for performing at least one of (i) forming a seal about a wound, and (ii) securing an article to skin. The method comprises identifying a wound or area of interest on a user's skin. The method also comprises providing an adhesive composition including a polysiloxane adhesive and at least one absorbent filler dispersed in the polysiloxane adhesive. And, the method additionally comprises providing a layer of the adhesive composition either (i) about the wound, or (ii) between the article and skin.

As will be realized, the subject matter is capable of other and different embodiments and its several details are capable of modifications in various respects, all without departing from the subject matter. Accordingly, the description is to be regarded as illustrative and not restrictive.

DETAILED DESCRIPTION OF THE EMBODIMENTS

Generally, in accordance with the subject matter, various preferred embodiment pressure sensitive adhesives are provided which comprise one or more absorbent fillers such as hydrocolloids dispersed in a silicone elastomeric matrix, which is preferably a silicone pressure sensitive adhesive composition. Also provided in accordance with the subject matter are a wide range of articles comprising the preferred embodiment pressure sensitive adhesives. In addition, various methods are provided for using the preferred embodiment compositions and articles.

The preferred embodiment pressure sensitive adhesive composition comprises a silicone pressure sensitive elastomer adhesive material having intimately dispersed therein a water soluble and/or swellable absorbent filler such as a hydrocolloid or mixture of hydrocolloids. The preferred embodiment pressure sensitive adhesive composition may also comprise one or more optional tackifier(s), one or more optional plasticizer(s), one or more optional additives, one or more optional fillers, and optional solvent.

Suitable absorbent fillers such as hydrocolloids include but are not limited to guar gum, xanthan gum, karaya gum, locus gum, polyvinyl alcohol, pectin, gelatin, carboxymethyl cellulose including sodium carboxymethyl cellulose and cross linked sodium carboxymethyl cellulose, high molecular weight carbowax, carboxypolymethylene, maize starch, alginic acid, and combinations thereof, with sodium carboxymethyl cellulose being preferred.

The absorbent filler such as a hydrocolloid or mixture of hydrocolloids should comprise from about 5 to about 60% by weight of the pressure sensitive adhesive composition and preferably from about 25% to about 35% by weight of the adhesive composition. However, it will be appreciated that in no way is the subject matter limited to these concentrations of the hydrocolloid(s). For example, compositions in accordance with the subject matter may include less than 5% hydrocolloid(s) and/or greater than 60% hydrocolloid(s).

Furthermore, instead of or in addition to one or more hydrocolloids, the subject matter includes the use of super absorbent materials. A preferred super absorbent material is a super absorbent polymer such as a polyacrylate super absorbent polymer. Super absorbent polymers (SAP) are polymers that can absorb and retain extremely large amounts of a liquid relative to their own mass. Water absorbing polymers, which are classified as hydrogels when cross-linked, absorb aqueous solutions through hydrogen bonding with water molecules. A SAP's ability to absorb water is a factor of the ionic concentration of the aqueous solution. In deionized and distilled water, a SAP may absorb 500 times its weight, i.e., from 30-60 times its own volume, but when incorporated into a 0.9% saline solution, the absorbency drops to approximately 50 times its weight. The presence of valence cations in the solution will impede the polymers' ability to bond with the water molecule. The total absorbency and swelling capacity are controlled by the type and degree of cross-linkers used to make the gel. Low density cross-linked SAP generally has a higher absorbent capacity and swells to a larger degree. These types of SAPs also have a softer and more adhesive gel formation. High crosslink density polymers exhibit lower absorbent capacity and swell, but the gel strength is firmer and can maintain particle shape even under modest pressure.

Super absorbent polymers are typically made from polymerization of acrylic acid blended with sodium hydroxide in the presence of an initiator to form a poly-acrylic acid sodium salt (sometimes referred to as sodium polyacrylate). This polymer is the most common type of SAP. Other materials are also used to produce a superabsorbent polymer, such as polyacrylamide copolymer, ethylene maleic anhydride copolymer, cross-linked carboxymethyl cellulose, polyvinyl alcohol copolymers, cross-linked polyethylene oxide, and starch grafted copolymer of polyacrylonitrile for example.

Silicone pressure sensitive adhesives are typically comprised of two major components, a siloxane polymer and a silicate resin. The siloxane polymers have alternating silicone and oxygen atoms along their main chain. They cover a wide range of molecular weights, ranging from about 170 g/mol to more than 1,000,000 g/mol. Examples of polymers used in silicone adhesives include polydimethylsiloxane, polymethylphenylsiloxane, polydimethyldiphenylsiloxane, and other silicone polymers including various organosiloxanes that are described generally as polysiloxanes. Silicones are generally hydrophobic, but they can be made less hydrophobic or more hydrophilic by modifying or copolymerizing them, for example, with alkylene oxides. Silicones and silicone adhesives are referred to herein interchangeably with the term polysiloxanes. An example of a silicate resin is tetrakis(trimethylsiloxy)silicate.

A cross-linked silicone adhesive may be comprised of a polyorganosiloxane and a silicate resin having a functionality of at least two sites capable of reacting with the polyorganosiloxane, optionally including plasticizers, for example, silicone oils including polydimethylsiloxane, optionally, also including non-hydrophilic organic or inorganic fillers, for example, amorphous precipitated silica as needed typically to obtain an elastic modulus in shear (G) between about $1 \times 10^4$ and $1 \times 10^7$ Pascal when measured at 25° C. and at shear rates between about 1 and 100 reciprocal seconds.

Alternatively, gels of silicone may also be used as the adhesive component of the preferred embodiment compositions. Silicone gels are generally formed from linear or branched silicone polymer having reactive groups thereon, as is known in the art. Such reactive groups undergo a crosslinking reaction during curing. Examples of crosslinking reactions include the hydrosilylation reaction in which a silicone having an Si—H reactive group reacts with a silicone having an aliphatically unsaturated reactive group in the presence of a platinum or rhodium catalyst. Alternatively, the reaction can involve the reaction of a silicone having an Si—OH reactive group with a silicone or a chain extender (e.g., a silane) having an alkoxy reactive group in the presence of a metal catalyst. A third possible gel may be formed from a silicone having an Si—OH containing polymer that is mixed with an alkoxysilane in the presence of a titanate catalyst.

In a preferred form of the subject matter, the adhesive is a polysiloxane available commercially under the trade name BIO-PSA from Dow Corning including the grade series BIO-PSA 7-4XXX. Suitable grades include 7-4101, 7-4102, 7-4103, 7-4201, 7-202, 7-4203, 7-4301, 7-4302, 7-4303, 7-4401, 7-4402, 7-4403, 7-4501, 7-4502, 4-4503, 7-4601, 7-4602, 7-4603. These are one-part adhesives that are cured (crosslinked) by the supplier and commercially available in a suitable solvent. Most preferred are 7-4602 and 7-4302. It is also contemplated that a combination of these preferred grades could be used. Optionally, additional fillers or plasticizers may be added. In a preferred form of the subject matter, the adhesive is a one part, pre-cured (crosslinked) adhesive that is essentially solvent free and referred to as a hot melt adhesive. In certain applications, a preferred adhesive formulation is obtained by blending one or more of the BIO-PSA silicone adhesives and the one or more hydrocolloids with powdered silica filler to adjust elastic modulus and so to also modify adhesion strength. Optionally, plasticizers including, for example, silicone oils such as polydimethylsiloxane may be added to improve moldability. Suitable formulations may in certain applications include up to about 50% silica or other fillers optionally including up to about 25% plasticizer.

Representative physical properties of the BIO-PSA silicone adhesives from Dow Corning are set forth below in Tables 1 and 2.

TABLE 1

Characteristics of BIO-PSA Adhesives

| | | Value | | | | | |
|---|---|---|---|---|---|---|---|
| Property | Unit | 7-4401 | 7-4501 | 7-4601 | 7-4402 | 7-4502 | 7-4602 |
| Nominal tack | | Low | Medium | High | Low | Medium | High |
| Value solvent | | Heptane | Heptane | Heptane | Ethyl acetate | Ethyl acetate | Ethyl acetate |
| Solid content | % | 60 | 60 | 60 | 60 | 60 | 60 |
| Viscosity | mPA · s | 450 | 700 | 1000 | 650 | 1500 | 2600 |
| Peel adhesion | g/cm | — | 700 | 500 | — | 700 | 500 |

TABLE 1-continued

Characteristics of BIO-PSA Adhesives

| Property | Unit | 7-4401 | 7-4501 | 7-4601 | 7-4402 | 7-4502 | 7-4602 |
|---|---|---|---|---|---|---|---|
| Shear | (kg/6.25 cm) | — | 16 | 15 | — | 16 | 15 |
| Rheology at 0.01 rad/sec at 30° C. (86° F.) | P | $5 \times 10^8$ | $5 \times 10^7$ | $5 \times 10^6$ | $5 \times 10^8$ | $5 \times 10^7$ | $5 \times 10^6$ |

TABLE 2

Characteristics of BIO-PSA Adhesives

| Property | Unit | 7-4101 | 7-4201 | 7-4301 | 7-4102 | 7-4202 | 7-4302 |
|---|---|---|---|---|---|---|---|
| Nominal tack Value solvent | | Low Heptane | Medium Heptane | High Heptane | Low Ethyl acetate | Medium Ethyl acetate | High Ethyl acetate |
| Solid content | % | 60 | 60/70 | 60/70 | 60 | 60 | 60 |
| Viscosity | mPA · s | 150 | 450/1100 | 500/1600 | 350 | 800 | 1200 |
| Peel adhesion | g/cm | — | 900 | 700 | — | 900 | 700 |
| Shear | (kg/6.25 cm) | 17 | 14 | — | 17 | 14 | — |
| Rheology at 0.01 rad/sec at 30° C. (86° F.) | P | $1 \times 10^9$ | $1 \times 10^8$ | $5 \times 10^6$ | $1 \times 10^9$ | $1 \times 10^8$ | $5 \times 10^6$ |

Another preferred silicone adhesive for use in the preferred embodiment compositions are those available from NuSil Technology under the designations DDR-1370 and DDR-4355. The DDR-1370 is a one-part non-curing traditional pressure sensitive adhesive dispersed in ethyl acetate. This adhesive has high cohesive strength and high release force, resulting in favorable temporary adhesive properties. The DDR-4355 is a transparent, silicone tacky gel which cures at low temperatures to a soft, high surface tack, temporary silicone adhesive. Typical characteristics of the DDR-1370 and DDR-4355 materials are set forth below in Tables 3 and 4.

TABLE 3

Characteristic of DDR-1370 Adhesive

| Properties | Average Result | Standard |
|---|---|---|
| Uncured: | | |
| Appearance | Translucent | ASTM D2090 |
| Viscosity | 1,450 cP (1,450 mPas) | ASTM D1084, D2196 |
| Non-Volatile Content | 65% | ASTM D2288 |
| FT-IR Spectroscopy (Identification) | Pass | — |
| Cured: 90 minutes @ 150° C. (302° F.) in oven, then 15 minutes @ 150° C. (302° F.) in heat press) | | |
| Release Force of PSA | 10 ppi (1.8 kN/m) | ASTM D1876 |
| PSA Blunt Probe Test | 1.5 lbs. (6.7 N) | ASTM D2979 |
| Tissue Culture (Cytotoxicity Testing) | Pass | USP <87> ISO 10993-5 |

TABLE 4

Characteristics of DDR-4355 Adhesive

| Properties | Average Result | Standard |
|---|---|---|
| Uncured: | | |
| Appearance | Translucent | ASTM D2090 |
| Viscosity | 1,500 cP (15,000 mPas) | ASTM D2196, D1084 |
| FT-IR Spectroscopy (Identification), Part A | Pass | — |
| FT-IR Spectroscopy (Identification), Part B | Pass | — |
| Cured: 3 hrs. @ 60° C. (140° F.) | | |
| Penetration (Lab Line Penetrometer, 19.5 g shaft, ¼ inch foot, 5 seconds) | 5 mm (0.20 inches) | — |
| Tissue Culture (Cytotoxicity Testing) | Pass | USP <87> ISO 10993-5 |

When utilizing a silicone adhesive, a solvent is typically selected from the group of alkanes, such as heptane; arenes, such as toluene; and esters, such as ethyl acetate; and combinations thereof. In this embodiment, the solvent serves as a processing aid, which is further described below. The silicone adhesive is typically present in at least about 40 parts by weight based on 100 parts of the silicone adhesive and the absorbent filler or hydrocolloid(s) combined. In certain applications, the silicone adhesive is typically present in an amount of from about 40 to about 95, and preferably from about 65 to about 75 parts by weight, based on 100 parts by weight of the composition. If a solvent is used, e.g., ethyl acetate, such solvent is typically present in an amount of 1 to 40, alternatively from 25 to 40, alternatively from 25 to 30, parts by weight, based on 100 parts by weight of the composition. However, it will be appreciated that in no way is the present subject matter limited to any of these concentrations or proportions of silicone component(s) and/or solvent(s).

As noted, the preferred compositions may comprise additional components. Suitable plasticizers or solvents include mineral oil and petrolatum with mineral oil being preferred. Terpene resin is a preferred tackifier. The silicone pressure sensitive adhesive serves as a binder for the hydrocolloid particles and, in addition, renders the final adhesive composition tacky, elastic, and pliable. In certain applications, it may also be preferable to also include an antioxidant such as butylated hydroxytoluene or butylated hydroxyanisole within the adhesive composition to prolong the shelf life of the composition and/or articles using the composition. Non-limiting examples of additives which may be included in the composition include laponite, cyclodextrin, kaolin, zinc oxide, silica, zeolite, silicone oil, siloxanes, silicone resins, SIS rubber, polyisobutylene, and combinations thereof. A wide array of various inorganic fillers can be used.

The preferred embodiment adhesive compositions are preferably used by forming a layer or region of the adhesive composition between a substrate such as biological skin and an article to be sealed and/or secured to the substrate. In most applications, a layer of the preferred adhesive composition has a thickness of from about 10 microns to about 1,000 microns, and preferably from about 50 microns to about 300 microns. However, it will be appreciated that in no way is the subject matter limited to any of these layer thicknesses. Furthermore, the adhesive compositions can be pattern coated, and/or used as fillers to fill voids and/or depressions in interfacing regions and particularly for providing sealing contact alongside human skin.

Additional details of the preferred embodiment compositions and mixtures of the silicone component(s) and solvent suitable(s) for making the composition are disclosed by various patents and publications including U.S. Pat. No. 4,882,377 to Sweet et al., U.S. Pat. No. 4,987,169 to Kuwata et al., U.S. Pat. No. 5,599,533 to Stepniewski et al., U.S. Pat. No. 5,654,362 to Schulz Jr. et al., U.S. Pat. No. 5,811,487 to Schulz Jr. et al., U.S. Pat. No. 5,880,210 to Schulz Jr. et al., U.S. Pat. No. 5,889,108 to Zhang, U.S. Pat. No. 5,929,164 to Zhang, U.S. Pat. No. 5,948,855 to Lin et al., U.S. Pat. No. 5,969,035 to Meinhardt et al., U.S. Pat. No. 5,977,280 to Kadlec et al., U.S. Pat. No. 5,994,459 to Berg et al., U.S. Pat. No. 6,015,858 to Gornowicz, U.S. Pat. No. 6,027,738 to Stepniewski et al., U.S. Pat. No. 6,080,394 to Lin et al., U.S. Pat. No. 6,168,782 to Lin et al., U.S. Pat. No. 6,177,071 to Lin et al., U.S. Pat. No. 6,200,581 to Lin et al., U.S. Pat. No. 6,207,717 to Lin et al., U.S. Pat. No. 6,221,927 to Lin et al., U.S. Pat. No. 6,221,979 to Lin et al., U.S. Pat. No. 6,238,657 to Lin et al., U.S. Pat. No. 6,346,583 to Kilgour et al., U.S. Pat. No. 6,444,745 to Kilgour et al., U.S. Pat. No. 6,538,061 to Chaiyawat et al., and U.S. Patent Application Publication No. 2004/0228821 to Sunkel et al., the disclosures of which are incorporated herein by reference in their entirety. It is to be appreciated that the compositions of the present subject matter may comprise any combination of one or more of the silicones, one or more of the hydrocolloids, and/or one or more of the solvents described and exemplified above.

Although the preferred embodiment compositions as described herein are contemplated to have a wide range of applications, a particularly preferred application is in negative pressure wound therapy (NPWT). Negative pressure wound therapy is a therapeutic technique using a vacuum dressing to promote healing in acute or chronic wounds and for example, enhance healing of first and second degree burns. The therapy involves the controlled application of sub-atmospheric pressure to the local wound environment, using a sealed wound dressing connected to a vacuum pump or other pressure reducing provision(s).

In NPWT, a wound is sealed to promote wound healing using sub-atmospheric pressure applied through a specialized dressing. The continued application of reduced pressure draws out edema from the wound, and typically increases blood flow to the area. The vacuum may be applied continuously or intermittently, depending on the type of wound being treated and the clinical objectives. Typically, the dressing is changed two to three times per week. The dressings used for the technique include open-cell foam dressings and gauze, sealed with an occlusive dressing intended to contain the sub-atmospheric pressure at the wound site. Where NPWT devices allow delivery of fluids, such as saline or antibiotics, to irrigate the wound, intermittent removal of used fluid supports the cleaning and drainage of the wound bed. The preferred embodiment compositions are particularly useful in NPWT and related articles such as dressings.

A particularly preferred article in accordance with the present subject matter is a dressing. The preferred embodiment dressings generally comprise a substrate or rigid or semi-rigid support member. Depending upon the intended use of the dressing, the substrate may be planar or non-planar; and/or flexible or deformable. Typically, a layer or region(s) of the preferred embodiment adhesive composition is disposed along a face or portion of the dressing substrate. In many applications, the dressing includes one or more viewing windows which provide visual inspection of an area covered by the dressing. Preferably, the viewing window(s) are covered by a transparent or light transmissive polymeric film. A wide array of such films are known in the art and may include for example polyurethane films. In certain applications, it may be preferred to select a film that exhibits relatively high moisture or water vapor transmission rates. Furthermore, as previously noted, in many applications the preferred embodiment dressings are used in NPWT applications. For these applications it is generally preferred that the dressing and/or the dressing substrate be sized, shaped and configured to provide an encapsulated volume above and around a wound, when the dressing is appropriately positioned. During NPWT, a reduced pressure will be maintained within the dressing and over the wound. Thus, the dressing must be formed from materials that maintain the shape and structure of the dressing and withstand forces applied from the higher pressure external atmosphere.

Although the subject matter is contemplated to find wide application in NPWT, it will be appreciated that in no way is the subject matter limited to such. Instead, the present subject matter will likely find use in a wide array of applications and particularly medical applications for contacting biological skin such as to adhesively retain or secure articles to a human patient and/or provide a seal about a targeted region on a patient's body.

The preferred embodiment compositions exhibit relatively high breathability such as characterized by a moisture vapor transmission rate (MVTR) of greater than 800 g/m$^2$/24 hours. The preferred embodiment compositions exhibit static absorption values of greater than 500 g/m$^2$/24 hours for a 100 μm thick layer. As noted, the preferred embodiment compositions exhibit excellent initial repositionability. This feature is exemplified by applying a dressing having a region of the preferred embodiment composition on skin with finger pressure. After 15 minutes, the dressing (and composition) is then removed and re-applied, and preferably repositioned. The dressing will be adhesively secured to its new position and remain secured to the user for typically three (3) days under normal conditions.

The preferred embodiment adhesive compositions can be used in a wide array of applications and particularly medical applications. The preferred embodiment adhesives, when applied to human skin under a variety of conditions, are repositionable and skin safe. Articles such as dressings and bandages containing layers or regions of the preferred embodiment adhesives can be repeatedly removed from skin, and re-applied as desired. Surprisingly, the preferred embodiment adhesives exhibit excellent tackiness and adhesiveness to human skin. Many known silicone based adhesives do not exhibit good adhesive characteristics when applied to human skin. These and other characteristics of the preferred embodiment adhesives enable their use in a variety of environments outside of a hospital arena. For example, the preferred embodiment adhesive compositions can be used at home or in home-based therapies.

Many other benefits will no doubt become apparent from future application and development of this technology.

All patents, applications, and articles noted herein are hereby incorporated by reference in their entirety.

As described hereinabove, the present subject matter solves many problems associated with previously known compositions and devices. However, it will be appreciated that various changes in the details, materials, and arrangements of components, which have been herein described and illustrated in order to explain the nature of the subject matter, may be made by those skilled in the art without departing from the principle and scope of the subject matter, as expressed in the appended claims.

What is claimed is:

1. An adhesive composition comprising:
   a polysiloxane adhesive,
   wherein the polysiloxane adhesive constitutes at least about 40% by weight of the adhesive composition; and
   one or more hydrocolloids dispersed in the polysiloxane adhesive,
   wherein the one or more hydrocolloids constitute from about 5% to about 60% by weight of the adhesive composition;
   wherein the polysiloxane adhesive is a one-part adhesive and at least partially crosslinked;
   wherein the polysiloxane adhesive is selected from the group consisting of (i) an adhesive having a solids content of about 60%, a viscosity of about 2600 mPA·s, and which exhibits a rheology at 0.01 rad/sec at 30° C. of about $5\times10^6$ P, (ii) an adhesive having a solids content of about 60%, a viscosity of about 1200 mPA·s, and which exhibits a rheology at 0.01 rad/sec at 30° C. of about $5\times10^6$ P, and (iii) a combination of (i) and (ii); and
   wherein the adhesive composition has a moisture vapor transmission rate (MVTR) of greater than 800 g/m²/24 hours.

2. The adhesive of claim 1 further comprising one or more absorbent fillers selected from the group consisting of guar gum, xanthan gum, karaya gum, locus gum, polyvinyl alcohol, pectin, gelatin, carboxymethyl cellulose, high molecular weight carbowax, carboxypolymethylene, maize starch, alginic acid, super absorbent polymers, and combinations thereof.

3. The adhesive of claim 2 wherein the one or more absorbent fillers constitute from about 25% to about 35% by weight of the adhesive composition.

4. The adhesive of claim 1 wherein the adhesive composition further comprises:
   at least one tackifier.

5. The adhesive of claim 1 wherein the adhesive composition further comprises:
   at least one plasticizer.

6. The adhesive of claim 1 wherein the adhesive composition further comprises:
   at least one additive.

7. The adhesive of claim 1 wherein the adhesive composition further comprises:
   at least one filler.

8. The adhesive of claim 1 wherein the adhesive composition further comprises:
   at least one solvent.

9. An article comprising a layer of an adhesive composition according to claim 1.

10. The article of claim 9 further comprising one or more absorbent fillers selected from the group consisting of guar gum, xanthan gum, karaya gum, locus gum, polyvinyl alcohol, pectin, gelatin, carboxymethyl cellulose, high molecular weight carbowax, carboxypolymethylene, maize starch, alginic acid, super absorbent polymers, and combinations thereof.

11. The article of claim 10 wherein the absorbent filler is carboxymethyl cellulose.

12. The article of claim 10 wherein the one or more absorbent fillers constitute from about 25% to about 35% by weight of the adhesive composition.

13. The article of claim 9 wherein the adhesive composition further comprises:
    at least one tackifier.

14. The article of claim 9 wherein the adhesive composition further comprises:
    at least one plasticizer.

15. The article of claim 9 wherein the adhesive composition further comprises:
    at least one additive.

16. The article of claim 9 wherein the adhesive composition further comprises:
    at least one filler.

17. The article of claim 9 wherein the adhesive composition further comprises:
    at least one solvent.

18. The article of claim 9 wherein the article is a dressing.

19. The article of claim 18 wherein the dressing further comprises a substrate on which the layer of the adhesive composition is disposed.

20. The article of claim 18 wherein the dressing defines at least one window providing viewing through the window.

21. The article of claim 20 wherein the dressing further comprises a thin barrier film extending over the at least one window and which allows transmission of light therethrough.

22. The article of claim 18 wherein the dressing is a NPWT dressing.

23. A method of sealingly securing an article to a substrate, the method comprising:
    providing an adhesive according to claim 1; and
    forming a layer of the adhesive composition between the article and the substrate.

24. The method of claim 23 wherein the substrate is biological skin.

25. The method of claim 23 wherein the method is used in negative pressure wound therapy.

26. The method of claim 23 wherein the layer of the adhesive composition is from about 50 microns to about 300 microns.

27. A method for performing at least one of (i) forming a seal about a wound, and (ii) securing an article to skin, the method comprising:
- identifying a wound or area of interest on a user's skin;
- providing an adhesive composition according to claim 1; and
- providing a layer of the adhesive composition either (i) about the wound, or (ii) between the article and skin.

28. The method of claim 27 wherein the layer of the adhesive composition is from about 50 microns to about 300 microns.

\* \* \* \* \*